(12) United States Patent
Kennedy et al.

(10) Patent No.: US 9,795,284 B2
(45) Date of Patent: *Oct. 24, 2017

(54) ENDOSCOPIC IMAGING SYSTEM AND METHOD FOR ADAPTING TO REMOTE STIMULUS

(71) Applicant: ARTHREX, INC., Naples, FL (US)

(72) Inventors: Bruce Laurence Kennedy, Santa Barbara, CA (US); Craig Speier, Santa Barbara, CA (US)

(73) Assignee: ARTHREX, INC., Naples, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/220,838

(22) Filed: Jul. 27, 2016

(65) Prior Publication Data

US 2016/0331217 A1 Nov. 17, 2016

Related U.S. Application Data

(63) Continuation of application No. 14/203,226, filed on Mar. 10, 2014, now Pat. No. 9,414,740.

(60) Provisional application No. 61/782,234, filed on Mar. 14, 2013.

(51) Int. Cl.
| A61B 1/045 | (2006.01) |
| A61B 1/00 | (2006.01) |
| H04N 5/232 | (2006.01) |
| H04N 5/225 | (2006.01) |

(52) U.S. Cl.
CPC .......... *A61B 1/045* (2013.01); *A61B 1/00006* (2013.01); *A61B 1/00009* (2013.01); *A61B 1/00016* (2013.01); *A61B 1/00039* (2013.01); *A61B 1/00045* (2013.01); *H04N 5/23203* (2013.01); *H04N 5/23206* (2013.01); *H04N 5/23225* (2013.01); *H04N 2005/2255* (2013.01)

(58) Field of Classification Search
CPC ............... A61B 1/045; H04N 5/23203; H04N 2005/2255; H04N 5/23206; H04N 5/23225; H04N 5/23216; G02B 23/243; G02B 23/2415; G06T 2207/10068
See application file for complete search history.

(56) References Cited

U.S. PATENT DOCUMENTS

| 6,120,435 A | 9/2000 | Eino |
| 6,496,099 B2 | 12/2002 | Wang et al. |
| 6,965,399 B1 | 11/2005 | Oka et al. |
| 9,414,740 B2 * | 8/2016 | Kennedy ................ A61B 1/045 |
| 2004/0124964 A1 | 7/2004 | Wang et al. |
| 2007/0050828 A1 | 3/2007 | Renzi et al. |
| 2009/0271243 A1 * | 10/2009 | Sholl .................... G06Q 30/018 434/365 |

(Continued)

*Primary Examiner* — Christopher K Peterson
(74) *Attorney, Agent, or Firm* — Karish & Bjorgum, PC

(57) ABSTRACT

A camera system having a camera head with at least one button; a camera control unit coupleable to the camera head, the camera unit having a network port for receiving requests or information from a remote user; a monitor coupleable to the camera control unit for displaying images from the camera head and information from the camera control unit; the at least one camera head button being configurable by the camera control unit to have a first function and reconfigurable by the camera control unit to have a second function upon receipt of a request or information from a remote user.

22 Claims, 3 Drawing Sheets

(56) References Cited

U.S. PATENT DOCUMENTS

2012/0200683 A1 8/2012 Oshima et al.
2014/0188435 A1* 7/2014 Coombs ................ G05B 23/00
                                                                              702/188

\* cited by examiner

ENDOSCOPIC IMAGING SYSTEM AND METHOD FOR ADAPTING TO REMOTE STIMULUS

CROSS REFERENCE TO RELATED APPLICATION

This application is a continuation application of U.S. patent application Ser. No. 14/203,226, filed on Mar. 10, 2014, entitled ENDOSCOPIC IMAGING SYSTEM AND METHOD FOR ADAPTING TO REMOTE STIMULUS, which claims priority of U.S. Provisional Patent Application No. 61/782,234, filed on Mar. 14, 2013, entitled ENDOSCOPIC IMAGING SYSTEM AND METHOD FOR ADAPTING TO REMOTE STIMULUS, the entire contents of both of which are hereby incorporated herein by reference.

BACKGROUND

The present invention relates to devices used in endoscopic surgery and, more particularly, to a user interface of an endoscopic imaging system.

During the course of endoscopic surgery the surgeon or staff may interact with an endoscopic video system to change system parameters. A typical user interface allows convenient control of parameters such as white balance, image zoom, or still image capture. To make parameter selections easily accessible to the surgeon most endoscopic video systems today include one or more buttons placed on the camera head. Some endoscopic systems may include a touch pad interface operable by surgical staff for parameter setting as a parallel backup to the camera head buttons. In currently marketed systems, user interface input, whether by the surgeon or staff, typically originates in the same room with the patient and endoscopic equipment.

Some newer endoscopic imaging equipment can interact with the world outside the operating room. One feature of these newer systems is the ability to stream video and audio to observers elsewhere in the hospital or across the Internet. These transmissions can be planned or spontaneous but preferably require notification of the surgeon and a grant of the surgeon's permission.

The surgeon needs a way to respond to requests for streaming video connections or other actions associated with the new wider reach of his equipment without unnecessarily complicating the user interface that has been designed for the specific purpose of endoscopic surgery. The medical surgical environment can quickly become hectic and require quick decisions and action so intuitive and simple user interfaces are desirable.

There exists a need to maintain the advantage of a simple user interface for a specific job while allowing the expansion of capability made necessary by today's network connected medical equipment.

SUMMARY

This invention describes an endoscopic imaging system with a simple user interface that reconfigures on stimulation from outside the operating room to at least temporarily accommodate external requests, and then revert back to its original operation.

The present invention, according to an embodiment is directed to a camera system having a camera head with at least one button; a camera control unit coupleable to the camera head, the camera control unit further comprising a network port for receiving requests or information from a remote user; a monitor coupleable to the camera control unit for displaying images from the camera head and information from the camera control unit; and wherein the at least one camera head button is configurable by the camera control unit to have a first function and reconfigurable by the camera control unit to have a second function upon receipt of a request or information from a remote user.

The first function may be, for example, selected from the group consisting of still image capture, video capture start, video capture stop, white balance, gain, brightness, zoom and image enhancement. The second function may be, for example, to accept a request from a remote user, manipulate an image or engage in a chat session. In an embodiment, the second function is maintained for a predetermined time period. Additionally, the camera control unit may be further configured to display indicia of the remote user request on the monitor and prompt an operator to accept the request by pressing the camera button.

In an additional embodiment, the camera head may have at least two buttons, each of the buttons being configurable by the camera control unit to have a unique first function and a unique second function upon receipt of a request or information from a remote user. Optionally, the second function of one of the buttons is to accept a request from a remote user and the second function of the other button is to deny the request from the remote user.

In an additional embodiment, the camera head further comprises at least four buttons oriented left, right, up and down, each of the buttons being configurable by the camera control unit to have a unique first function and a unique second function upon receipt of a request or information from a remote user. Optionally, the camera head buttons are each configured to have a second function wherein the buttons cause movement of a symbol to a different location on an image displayed on the monitor.

The present invention, according to another embodiment is directed to a camera system comprising: a camera control unit coupleable to a camera head, the camera control unit further comprising a network port for receiving a request or information; an input device in communication with the camera control unit; and a display coupleable to the camera control unit for displaying images from the camera head and information from the camera control unit. The input device is configurable by the camera control unit to have a first function and reconfigurable by the camera control unit to have a second function upon receipt of the request or information.

Optionally, the input device may be selected from the group consisting of: a camera head button, a foot switch and a hands free gesture recognition system. The first function may be selected from the group consisting of still image capture, video capture start, video capture stop, white balance, gain, brightness, zoom and image enhancement. The second function may be to accept a request from a remote user. In an embodiment, the second function is maintained for a predetermined time period. Optionally, the camera control unit is further configured to display indicia of the request or information on the display and prompt an operator to accept the request or acknowledge the information using the input device. In an embodiment, the input device is reconfigurable by the camera control unit to have a third function different from the first function and the second function after receiving input from a user.

The present invention, according to an embodiment, is also directed to a method for allowing a user to interact with a camera system comprising a camera head with at least one user operated button and a camera control unit, the camera control unit further comprising a network port for receiving requests or information from a remote user, the method comprising the steps of: configuring the at least one camera head button to have a first function when operated by a user; receiving by the camera control unit of a request or information from a remote user; and reconfiguring the at least one camera head button to have a second function different from the first function.

Additionally, the method may have the step of further reconfiguring the at least one camera head button to the first function after a predetermined period of time. Additionally, the method may have the step of further reconfiguring the at least one camera head button to the first function after receiving input from the user. Additionally, the method may have the step of further reconfiguring the at least one camera head button to a third function different from the first function and the second function after receiving input from user.

BRIEF DESCRIPTION OF THE DRAWINGS

The features, aspects and advantages of the present invention will become better understood with regard to the following description, appended claims and accompanying figures wherein:

DETAILED DESCRIPTION

In the following description of the preferred embodiments, reference is made to the accompanying drawings which show by way of illustration specific embodiments in which the invention may be practiced. Wherever possible, the same reference numbers will be used throughout the drawings to refer to the same or like parts. It is to be understood that other embodiments may be utilized and structural and functional changes may be made without departing from the scope of the present invention.

Figure 1:
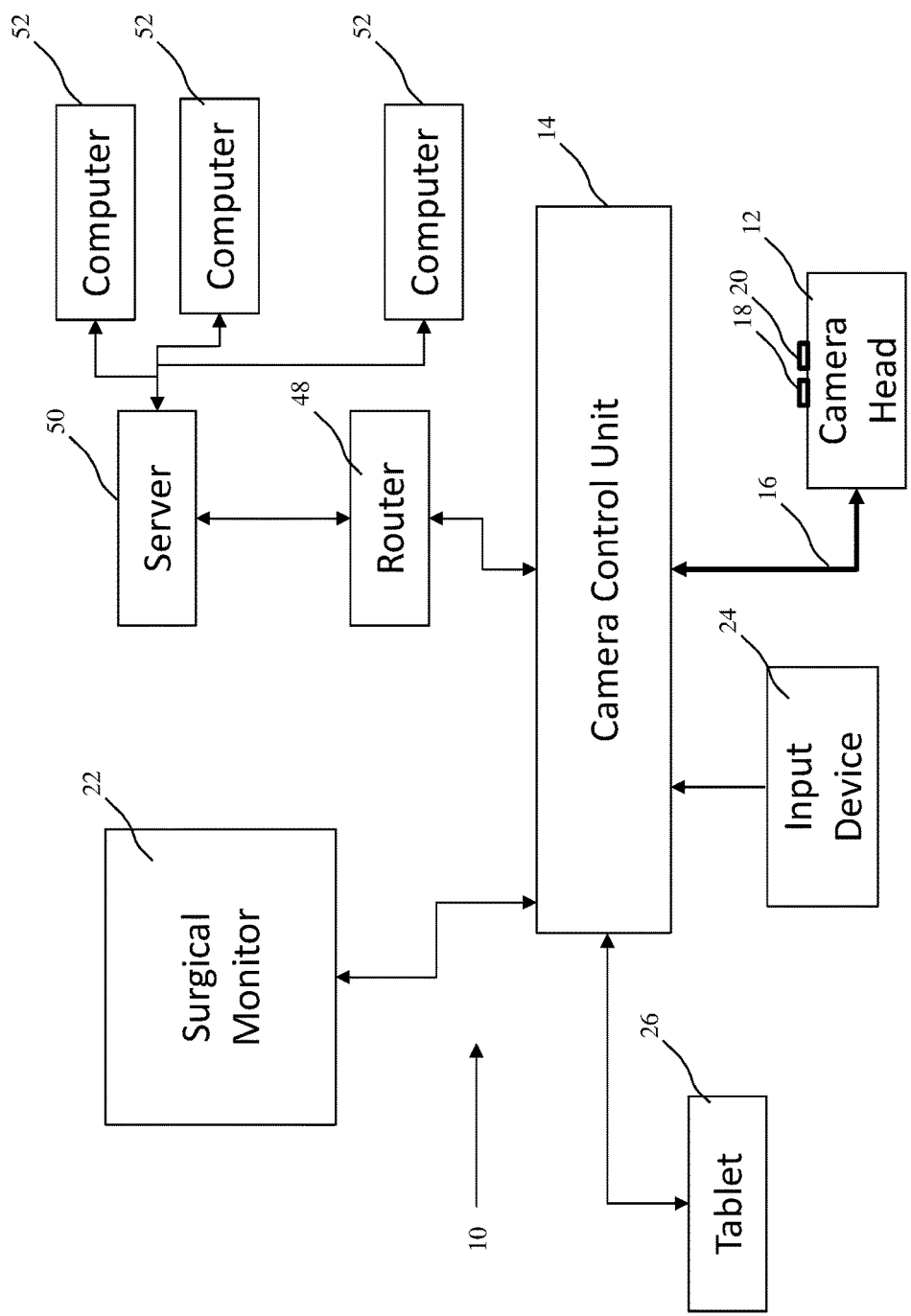
FIG. 1 is a schematic diagram illustrating an imaging system for adapting to a remote stimulus according to an embodiment of the present invention.

A endoscopic imaging system 10 for adapting to a remote stimulus according to an embodiment of the present invention is shown in FIG. 1. The endoscopic imaging system 10 allows for internal features of a body of a patient to be viewed without the use of traditional, fully invasive surgery. Additionally, the endoscopy system may be used for imaging of hard to reach parts of structures or in other applications where direct optical viewing is compromised.

The endoscopic imaging system 10 has a camera head 12 and a camera control unit 14. In an embodiment, the camera head 12 is coupled to the camera control unit 14 via a cable 16 to facilitate data transfer between the camera head 12 and the camera control unit 14. In an alternative embodiment, the camera head 12 is wirelessly coupled to the camera control unit 14 such as via IEEE 802.11b, or IEEE 802.11n or ultra-wide band (UWB).

The camera head 12 acquires image data and transmits it to the camera control unit 14 to process a usable image. The camera head 12 may be used together with an endoscope or other medical instruments for transmitting image data. The camera head 12 may include one or more imaging devices, utilizing a variety of technology types. For example, the imaging devices may include one or more charge coupled device (CCD) sensors or complementary metal-oxide-semiconductor (CMOS) sensors. The camera head 12 may further include an illumination system. The camera head 12 may also have memory for storing camera data, camera control unit processing data or other information.

The camera head 12 has at least one user input means, such as a button, to control aspects of image capture. In a preferred embodiment of the present invention, the camera head 12 has a first button 18 and a second button 20 for controlling aspects of image capture and, as will be further described below, for variably controlling other performance aspects of the imaging system.

The camera control unit 14 is coupled to a monitor 22 where image data is displayed for a surgeon. The camera control unit 14 may overlay the image data with additional information for the surgeon as will be discussed further below. The camera control unit 14 is also connectable to at least one input device 24 such as a mouse, keyboard, foot switches, touchpad, hands free gesture recognition system or touchscreen monitor. Additionally, the camera control unit 14 may be connectable to a tablet computer 26, such as an Apple® iPad®.

Figure 2:
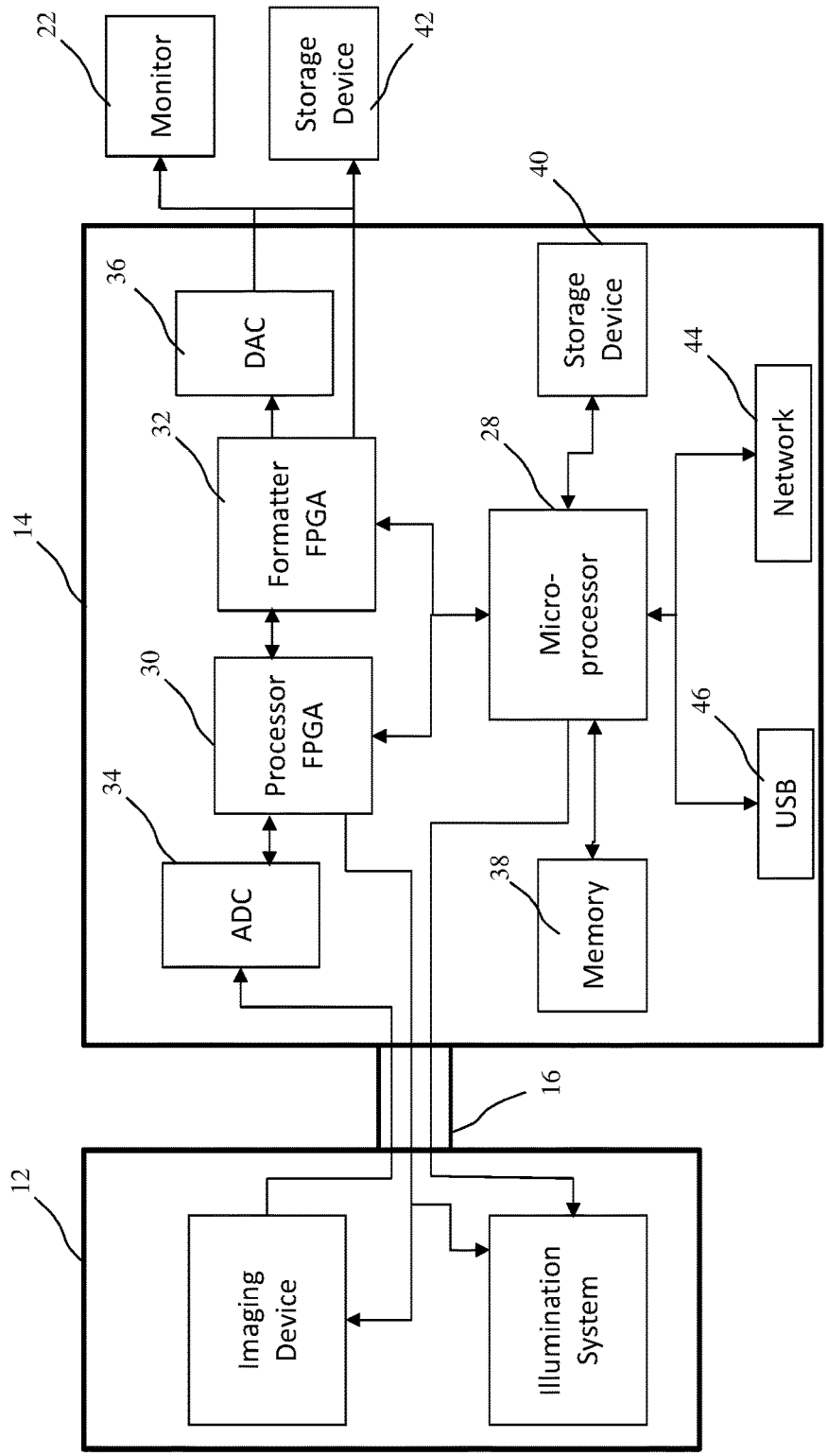
FIG. 2 is a schematic diagram illustrating a camera head and camera control unit usable in the imaging system of FIG. 1.

As shown in FIG. 2, the camera control unit 14 contains a microprocessor 28 for interfacing with user input devices 24, a signal processing circuit 30, a signal formatting circuit 32, analog to digital converters 34, digital to analog converters 36 and memory 38. The camera control unit 14 runs program applications providing for a variety of capabilities. For example, the camera control unit 14 may provide for a live feed of the image generated by the camera head 12 to be displayed through the monitor 22. Additionally, the camera control unit 14 may provide image capture functionality allowing for images generated by the camera head 12 to be saved to a storage device, such as an internal storage device 40 or a storage device 42 external to the camera control unit. The captured images may be annotated and/or edited and displayed through the monitor 22.

In an embodiment, the camera control unit 14 also has at least one network interface 44 which may be a wired interface such as Ethernet, or a wireless network connection that allows for the camera control unit 14 to access a network. Optionally, the network interface 44 allows the camera control unit 14 to access the Internet.

The camera control unit 14 may be programmed to act as a web host, thereby allowing remote control of the camera control unit, such as via a web browser. This may allow the camera control unit to be accessed anywhere within a local network, or if allowed, from anywhere on the Internet, and both programmed and monitored. For example, with reference to FIG. 1, through the network interface 44, the camera control unit 14 may be directly or indirectly connected to a router 48, a server 50 or one or more computers 52 to allow for the exchange of information between the camera control unit and remotely located users. Computers 52 may also include mobile computing devices, such as tablets, cellular phones and laptop computers. This may also allow for streaming video of a procedure to be observed in real-time anywhere in the world. In an embodiment, when streaming is taking place, an indication is made on the monitor 22.

In an embodiment, the external storage device 42 may be, for example, a flash memory storage device or a hard disk storage device, and may be connected to the camera control unit 14 through a USB connection 46 or firewire connection (not shown). In an embodiment, a program application for the camera control unit, or data relevant to a particular patient or surgeon, is stored on the external storage device 42 and may be used to quickly configure the camera control unit for future sessions. Preferably, the camera control unit 14 can save images and video in different formats and to different places (e.g. internal memory, an external memory, or to a remote location over the Internet).

In an embodiment, the camera head buttons 18 and 20 have preselected functions when pressed. The preselected functions for a given camera head operator (e.g. surgeon) may be saved as part of a surgeon profile and stored, such as in the internal storage device 40, external storage device 42 or on the server 50 or computer 52 so that the operator may anticipate the functionality of the system and the system may be quickly configured for the operator's preferences.

Each of the first and second camera head buttons 18, 20 may be configured to control, for example and without limitation, still image capture, video capture start, video capture stop, white balance, gain, brightness, zoom and image enhancement. The amount of gain, brightness, zoom and image enhancement may be preset to different levels depending on surgeon preferences. When an operator presses the first or second camera head buttons 18, 20 a signal is sent to the camera control unit 14 and causes the camera control unit 14 to perform the desired function.

The function of the first and second camera head buttons 18, 20 may be varied by the camera control unit 14 upon predetermined environmental or system changes. Operation of a system wherein camera head button functionality may be varied according to an embodiment of the present invention will now be described with reference to FIG. 3.

Figure 3:
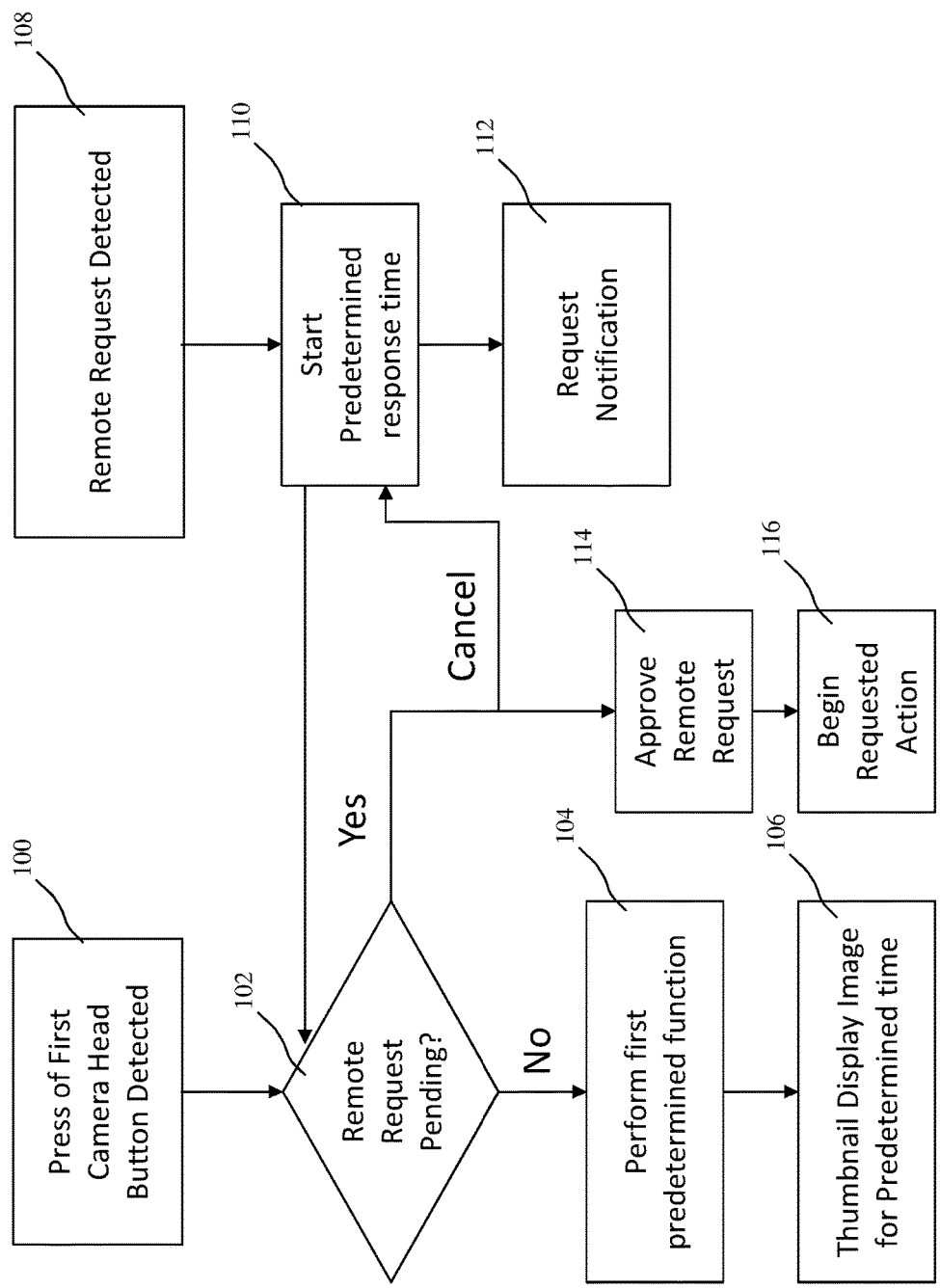
FIG. 3 is a chart showing the program flow of a user interface according to an embodiment of the present invention wherein the left camera head button is configured to have a default function of triggering still image capture and a different function of approving a request when the camera control unit receives a remote request for video streaming.

As shown in FIG. 3, if a press of the first button is received by the camera control unit (Box 100), the camera control unit checks to see if a remote request is pending (Box 102). If no remote request is pending, then the camera control unit causes the press of the first button to perform its default predetermined function, e.g. capture a still image (Box 104) and display the still image on the monitor 22 for a predetermined time, such as 5 seconds (Box 106).

If a remote input or request is received by the camera control unit 14 (Box 108), such as through the network port 44, then the camera control unit sets a predetermined response time during which the function of one or more of the camera head inputs (e.g. the first camera head button 18) will be changed to respond to the input or request (Box 110). For example, the first camera head button 18 may have altered functionality to "accept" the request for 10 seconds, 30 seconds or 1 minute.

If no button press is detected within the predetermined response time, then the functionality of the camera head buttons 18 is returned to the state prior to receipt of the input or request. In an additional embodiment, if a button press is detected within the predetermined time (Box 104), then functionality of the camera head buttons is returned to the state prior to receipt of the input or request. In an additional embodiment, depending on the nature of the input or request and the response by the operator, the functionality of the camera head buttons may then be changed to have still other functionality. In an additional embodiment, when a remote input or request is received by the camera control unit the functionality of the camera head buttons may be changed for an unlimited time, such as until a response is received from a user.

In addition, according to an embodiment, once a remote input or request, (e.g. request for video streaming) is received by the camera control unit 14 (Box 108), a notification is generated informing the operator of the input or request and prompting the operator to respond, such as by using the camera head inputs (Box 112). In an embodiment, the notification is a graphic overlay displayed on the surgical monitor 22. In an alternative embodiment, the notification is an audio message, such as a spoken phrase or beep emitted by for example a speaker in the camera control unit or surgical monitor.

If a press of the first camera head button 18 is detected (Box 100) after a remote request is received (Box 108) and within the predetermined response time (Box 110), then the camera control unit accepts the remote request (Box 114) and begins the requested action (for example starts streaming video to the remote user) (116). Additionally, the first camera head button 18 may be configured to deny the remote request if pressed during the predetermined response time. If the first camera head button 18 is configured to deny the request and a press of the first camera button is received during the predetermined response time, the response time period is terminated, the requester is notified of the denial and the function of the first camera head button is returned to its default function.

Illustrative examples will now be described with reference to specific camera head button functionality and specific remote requests. These examples are not intended to limit the functionality of the systems or steps in the methods disclosed herein.

EXAMPLE 1

In a first example, the camera control unit 14 is configured so that in a default state when an operator presses the first head button 18 the camera control unit captures a still image from the camera head 12, displays the still image on the surgical monitor 22 for a predetermined display time and saves the image to a storage device, such as internal storage device 40. Upon receipt of a request from a remote user to be granted access to streaming video at a remote location, the camera control unit displays a message on the surgical monitor 22 prompting the operator to approve the request by pressing the first head button 18.

The camera control unit sets a timer for 15 seconds in which the operator may press the first head button 18 to approve the request. If no button press is received within 15 seconds, then the request is denied and operation of the first head button 18 is returned to still image capture. If the first head button 18 is pressed within the 15 seconds, then the camera control unit 14 allows video to be streamed to the remote user and functionality of the first head button is returned to still image capture.

EXAMPLE 2

In a second example, the camera control unit 14 is configured so that in a default state when an operator presses the first head button 18 the camera control unit captures a still image from the camera head 12, displays the still image on the surgical monitor 22 for a predetermined display time and saves the image to a storage device, such as internal storage device 40. The camera control unit 14 is further configured so that in a default state when an operator presses the second head button 20, the camera control unit causes image enhancement. Upon receipt of a request from a remote user to be granted access to streaming video at a remote location, the camera control unit displays a message on the surgical monitor 22 prompting the operator to approve the request by pressing the first head button 18 and deny the request by pressing the second head button 20.

The camera control unit sets a timer for 15 seconds in which the operator may press the first head button 18 to approve the request or the second head button 20 to disapprove the request. If no button press is received within 15 seconds, then the request is denied, operation of the first head button 18 is returned to still image capture and operation of the second head button is returned to image enhancement. If the first head button 18 is pressed within the 15 seconds, then the camera control unit 14 allows video to be streamed to the remote user and functionality of the first head button is returned to still image capture. If the second head button 20 is pressed within the 15 seconds then the request is denied, the first head button is returned to still image capture and the second head button is returned to image enhancement.

EXAMPLE 3

The camera head 12 has four buttons configured in a left, right, up and down orientation, each button having a separate default function selected from still image capture, video capture start, video capture stop, white balance, gain, brightness, zoom and image enhancement. Upon receipt of a request from a remote user asking that a particular structure in the image be indicated, the camera control unit 12 displays an indicator graphic on the surgical monitor 22 and prompts the operator to move the graphic to a particular location on the image using the camera head buttons. After a preset time or action all buttons return to their original function and the graphic disappears.

EXAMPLE 4

In a fourth example, the camera control unit 14 is configured so that in a default state when an operator presses the first head button 18 the camera control unit captures a still image from the camera head 12, displays the still image on the surgical monitor 22 for a predetermined display time and saves the image to a storage device, such as internal storage device 40. Upon receipt of a request from a remote user to add annotations to the image displayed on the surgical monitor, the camera control unit displays a message on the surgical monitor 22 prompting the operator to approve the request by pressing the first head button 18.

The camera control unit sets a timer for 15 seconds in which the operator may press the first head button 18 to approve the request. If no button press is received within 15 seconds, then the request is denied and operation of the first head button 18 is returned to still image capture. If the first head button 18 is pressed within the 15 seconds, then the camera control unit 14 allows the observer at the remote location (such as a remote user operating a tablet) to add annotations over the live video and displays the annotations on the surgical monitor 22 for consideration by the operator. After a button press, remote observer action, or time out, the camera control unit 12 clears the annotation from the image displayed on the surgical monitor 22 and returns functionality of the first head button to still image capture.

EXAMPLE 5

In a fifth example, the camera control unit 14 is configured so that in a default state when an operator presses the first head button 18 the camera control unit captures a still image from the camera head 12, displays the still image on the surgical monitor 22 for a predetermined display time and saves the image to a storage device, such as internal storage device 40. Upon receipt of a request from a remote user to chat with the operator, the camera control unit displays a message on the surgical monitor 22 prompting the operator to approve the request by pressing the first head button 18.

The camera control unit sets a timer for 15 seconds in which the operator may press the first head button 18 to approve the request. If no button press is received within 15 seconds, then the request is denied and operation of the first head button 18 is returned to still image capture. If the first head button 18 is pressed within the 15 seconds, then the camera control unit 14 allows the remote user to submit text messages to the surgeon. Upon receipt of text messages, the camera control unit 12 displays the text messages (preferably along with the remote user's identity) on the surgical monitor 22. Preferably, the text messages are presented unobtrusively outside of the main endoscopic image.

Optionally, multiple different remote users can text the operator at the same time, with each remote user obtaining approval in a similar manner. Optionally, the text messages are included with any outgoing streamed video so that remote viewers can see the text messages. Optionally, the text messages are included on recorded video so that later viewers can see the text messages. Optionally, the operator may respond to text messages via a microphone connected to the camera control unit 12 with the audio being streamed to remote users along with any streamed video. This unidirectional text and audio connection provides hands-free communication between the surgeon and one or more observers and is especially valuable for medical education.

Optionally, after the text session is enabled, the first head button or another head button is reconfigured to end the chat session. Upon receipt of a button press of the button configured for ending the chat session, the chat session is terminated, any text messages removed from the surgical monitor, the microphone disabled, and the camera head buttons returned to their default configuration.

While the above illustrations are for camera head buttons, the system may also work with other input devices 24. A foot switch may be configured to have a preselected function when pressed. As with the camera head buttons, the preselected function may be saved for a given camera head operator. The foot switch may be configured to control, for example and without limitation, still image capture, video capture start, video camera stop, white balance, gain, brightness, zoom and image enhancement. The function of the switch may be varied by the camera control unit 14 upon predetermined environmental or system changes.

There is disclosed in the above description and the drawings, an imaging system that fully and effectively overcomes the disadvantages associated with the prior art. However, it will be apparent that variations and modifications of the disclosed embodiments may be made without departing from the principles of the invention. The presentation of the preferred embodiments herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. §112.

What is claimed is:

1. A camera system comprising:
a camera head comprising at least one button;
a camera control unit coupleable to the camera head, the camera control unit further comprising a network port for receiving requests or information from a remote user;
a monitor coupleable to the camera control unit for displaying images from the camera head and information from the camera control unit; and
wherein the camera control unit is configured so that the at least one camera head button both a first function and a second function different than the first function upon receipt of a request or information from a remote user; and
wherein the second function is to deny a request from a remote user.

2. The camera system of claim 1 wherein the first function is selected from the group consisting of still image capture, video capture start, video capture stop, white balance, gain, brightness, zoom and image enhancement.

3. The camera system of claim 2 wherein the second function is maintained for a predetermined time period.

4. The camera system of claim 3 wherein the camera control unit is further configured to display indicia of the remote user request on the monitor and prompt an operator to deny the request by pressing the at least one camera head button.

5. The camera system of claim 3 wherein the camera control unit further comprises a speaker and the camera control unit is further configured to generate at least one of a sound and an audio message through the speaker to indicate the remote user request and prompt an operator to deny the request by pressing the at least one camera head button.

6. A method for allowing a user to interact with a camera system comprising a camera head, at least one input device and a camera control unit, the camera control unit further comprising a network port for receiving requests or information from a remote user, the method comprising the steps of:
configuring the camera control unit so that the at least one input device has both a first function when operated by a user and a second function different from the first function upon receipt of a request or information from a remote user.

7. The method of claim 6 wherein the at least one input device is selected from the group consisting of: a camera head button, a mouse, a foot switch, a touchpad, a tablet computer and a hands free gesture recognition system.

8. The method of claim 6 wherein the step of configuring the camera control unit further comprises configuring the camera control unit so that the at least one input device reverts to the first function after a predetermined period of time.

9. The method of claim 6 wherein the step of configuring the camera control unit further comprises configuring the camera control unit so that the at least one input device reverts to the first function after receiving input from the user.

10. The method of claim 6 wherein the step of configuring the camera control unit further comprises configuring the camera control unit so that the at least one input device has a third function different from the first function and the second function after receiving input from the user.

11. A camera system comprising:
a camera head;
a camera control unit coupleable to the camera head, the camera control unit further comprising a network port for receiving requests or information from a remote user;
a monitor coupleable to the camera control unit for displaying images from the camera head and information from the camera control unit; and
an input device coupled to the camera control unit for transmitting a signal to the camera control unit; and
wherein the camera control unit is configured so that the at least one input device has both a first function and a second function different than the first function upon receipt of a request or information from a remote user; and
wherein the first function is selected from the group consisting of still image capture, video capture and image enhancement.

12. The camera system of claim 11 wherein the input device is selected from the group consisting of: a camera head button, a mouse, a foot switch, a touchpad, a tablet computer and a hands free gesture recognition system.

13. The camera system of claim 12 wherein the camera control unit is configured so that the first function is still image capture and when an operator engages the input device, the camera control unit captures a still image from the camera head, displays the still image on the monitor, and saves the image to a storage device.

14. The camera system of claim 13 wherein the second function is to accept an annotation request from a user; the camera control unit is configured so that upon request from a remote user to add annotations to the image displayed on the monitor, the camera control unit displays a message on the monitor prompting the operator to approve the request using the input device; and wherein the camera control unit is further configured so that if a signal is received from the input device during a predetermined time after receipt of the request from the remote user, the remote user is enabled to add annotations on the surgical monitor for consideration by the operator.

15. The camera system of claim 14 wherein if no signal is received from the input device during the predetermined time after receipt of the request from the remote user then the request is denied and the input device reverts to the first function.

16. The camera system of claim 13 wherein the second function is to accept a text message request from a user; the camera control unit is configured so that upon request from a remote user to communicate with the operator via text message, the camera control unit displays a message on the monitor prompting the operator to approve the request using the input device; and wherein the camera control unit is further configured so that if a signal is received from the input device during a predetermined time after receipt of the request from the remote user, the remote user is enabled to communicate with the operator via text message.

17. The camera system of claim 16 wherein the camera control unit is further configured to display text messages from a remote user on the monitor.

18. The camera system of claim 17 wherein the camera control unit is further configured to record video from the camera head along with text messages from a remote user.

19. The camera system of claim 17 wherein the camera control unit is further configured to stream video from the camera head over a network along with text messages from a remote user.

20. The camera system of claim 17 wherein the camera control unit is further configured so that the input device has a third function upon approval of a request to communicate via text message and wherein the third function is to end text messaging with a remote user.

21. The camera system of claim 16 wherein multiple remote users may be enabled to communicate with the operator via text message and wherein the camera control unit is further configured to display the name of each remote user along with text messages from remote users.

22. The camera system of claim 16 wherein if no signal is received from the input device during the predetermined time after receipt of the request from the remote user then the request is denied and the input device reverts to the first function.

* * * * *